United States Patent
Schulz

(10) Patent No.: US 8,360,978 B2
(45) Date of Patent: Jan. 29, 2013

(54) ULTRASOUND DEVICE FOR MEDICAL APPLICATIONS

(75) Inventor: Michael Clossen-von Lanken Schulz, Geldern (DE)

(73) Assignee: Siemens Aktiengesellschaft, Munich (DE)

( * ) Notice: Subject to any disclaimer, the term of this patent is extended or adjusted under 35 U.S.C. 154(b) by 793 days.

(21) Appl. No.: 12/159,642

(22) PCT Filed: Nov. 20, 2006

(86) PCT No.: PCT/EP2006/068651
§ 371 (c)(1),
(2), (4) Date: Sep. 28, 2009

(87) PCT Pub. No.: WO2007/077051
PCT Pub. Date: Jul. 12, 2007

(65) Prior Publication Data
US 2012/0029352 A1 Feb. 2, 2012

(30) Foreign Application Priority Data
Jan. 5, 2006 (DE) .......................... 10 2006 000 838

(51) Int. Cl.
*A61B 8/00* (2006.01)
(52) U.S. Cl. ........ 600/439; 600/437; 600/443; 600/447; 600/459; 601/2; 382/152
(58) Field of Classification Search .................. 600/437, 600/439, 443, 447, 459; 382/152; 601/2
See application file for complete search history.

(56) References Cited

U.S. PATENT DOCUMENTS

| 5,720,286 | A | 2/1998 | Chapelon et al. |
| 5,762,616 | A | 6/1998 | Talish |
| 6,678,403 | B1 * | 1/2004 | Wilk .............................. 382/152 |
| 6,980,688 | B2 * | 12/2005 | Wilk .............................. 382/152 |
| 7,497,828 | B1 * | 3/2009 | Wilk et al. ..................... 600/443 |
| 7,597,665 | B2 * | 10/2009 | Wilk et al. ..................... 600/459 |
| 2004/0139801 | A1 * | 7/2004 | Wilk .............................. 73/627 |
| 2005/0020918 | A1 * | 1/2005 | Wilk et al. ..................... 600/439 |
| 2005/0060012 | A1 | 3/2005 | Voorhees et al. |
| 2008/0228077 | A1 * | 9/2008 | Wilk et al. ..................... 600/447 |
| 2008/0269647 | A1 * | 10/2008 | Brunsveld Van Hulten ...... 601/2 |
| 2012/0029352 | A1 * | 2/2012 | Schulz .......................... 600/439 |

FOREIGN PATENT DOCUMENTS

| DE | AT 294 301 | 11/1971 |
| DE | 27 11 098 | 4/1980 |
| DE | 22 60 257 B2 | 5/1980 |
| DE | 20 2004 002 930 U1 | 6/2004 |
| DE | 20 2004 006 536 U1 | 2/2005 |
| WO | WO 97/29699 | 8/1997 |
| WO | WO 01/00084 | 1/2001 |
| WO | WO 02/43805 | 6/2002 |
| WO | WO 02/44753 | 6/2002 |
| WO | WO 2005/061053 | 7/2005 |

* cited by examiner

Primary Examiner — Tse Chen
Assistant Examiner — Baisakhi Roy
(74) Attorney, Agent, or Firm — Schiff Hardin LLP

(57) ABSTRACT

An ultrasound device for medical application has a transducer formed by a number of transducer elements. The transducer elements are carried on a flexible support that allows the transducer elements to be configured to an examination subject. A measurement device determines, for each transducer element, a distance or a rotation thereof with respect to a reference point. The reference point can be a point that is physically a part of the ultrasound device, or can be a virtual reference point.

12 Claims, 2 Drawing Sheets

ULTRASOUND DEVICE FOR MEDICAL APPLICATIONS

BACKGROUND OF THE INVENTION

1. Field of the Invention

The present invention concerns an ultrasound device for medical applications, of the type having a transducer formed by multiple transducer elements, wherein the transducer elements are housed in a flexible carrier.

2. Description of the Prior Art

At present, ultrasound devices are widely used in medical technology for diagnostic questions, for example in cardiology in which image exposures or films of the heart are generated with ultrasound. A further application field is lithotripsy, in which the sound waves are used to identify kidney and gall stones.

In principle, ultrasound technology is of interest for the treatment of tumors, based on focusing the ultrasound onto one or more points at which a high energy density that should destroy the tumor would then be generated. However, it has previously not been possible to use ultrasound for this purpose since the body parts on which the transducer would have to be placed (such as, for example, the head of a human or animal patient) are not flat but curved, and the curvatures are specific to the patient and therefore are individual. A controlled sound intromission is therefore not possible with the presently existing ultrasound devices. However, the precision of the treatment is a basic requirement given a use in combating tumors since the patient could otherwise suffer irreparable harm. The high energy density should be confined only to points at which tumor tissue exists, that must be destroyed.

For these reasons, treatment of tumors has previously not occurred using ultrasound but rather exclusively operatively, with x-ray radiation or chemically.

An ultrasound transducer arrangement in which additional transducers are arranged in a circle around a central transducer is known from DE 22 60 257, wherein a flexibly fashioned carrier is provided with a middle part and at least three flexible arms extending like rays from the middle part; a reception transducer attached in the middle part; and transmission transducers respectively attached at the ends of the arms.

SUMMARY OF THE INVENTION

An object of the present invention is provide an ultrasound device that is improved with regard to the known ultrasound devices and enables the use of ultrasound in previously inaccessible medical fields, in particular for tumor treatment.

To achieve this object, an ultrasound device of the aforementioned type is provided that has a measurement device that is fashioned to determine the distances and the rotations of the transducer elements relative to a reference point, in particular relative to a reference point provided at the ultrasound device and/or relative to a virtual reference point.

The transducer elements (sometimes also called transceiver elements) that are fashioned at least for transmission of ultrasound (possibly for transmission and reception of ultrasound) are incorporated into a flexible carrier element, instead of the previous flat and rigid arrangements of transducer elements. The transducer elements for transmission or reception of the sound waves are incorporated into a carrier matrix such that a person-specific adaptation to the surface on which the elements lie is enabled due to the flexibility of this carrier. A controlled sound intromission into the body is thereby possible.

As noted, the ultrasound device has a measurement device that is fashioned to determine the distances and the rotations of the transducer elements relative to a reference point, in particular relative to a reference point provided on the ultrasound device and/or a virtual reference point. A determination of the parameterization for the implementation of the examination or the treatment with ultrasound device is thereby possible. An arbitrary point on the apparatus can be provided as a reference point, or a purely virtual reference point that merely serves as a reference point for the specification of distances and positions of the individual transducer elements. An exact position determination that ultimately enables a controlled sound intromission into the body of the patient is possible with the use of the reference point and the measurement device that, with the use of a control device, identifies the positions of the individual elements from the received sound from a test series according to which the individual transducer elements emit sound waves. For example, if not all transducer elements are used for a treatment, the measurement device can determine the distances and rotations only of the required elements.

The sound intromission angle and/or a focus point can be electronically adjustable and/or variable and/or definable for at least one (in particular all) transducer elements by means of a control device of the ultrasound device, in particular dependent on specifications of an operator. The ultrasound device is advantageously fashioned in the phased array technique in which the many small transducer elements of the transducer can be individually electronically adjusted relative to their sound intromission angle and focus points. For this purpose, an operator (for example a physician or medical technology assistant) can input the basic specifications through the control device that can be operated via a monitor or via a display with an input device, with which specifications the control device (possibly automatically) calculates the sound intromission angle or, respectively, the focus point or even multiple focus points.

This means that the physician operating the ultrasound device selects (for example using an anatomical exposure of the patient) a point of a tumor at which a treatment should occur via radiation of a high energy density. From this the control device determines the required sound intromission angles and the focus point using the patient-specific position of the transducer elements that is provided by the placement of the flexible carrier in the treatment region on the body of the patient and sets the required sound intromission angles and the focus point. The sound intromission angles can be altered, for example in order to continue the treatment in an adjoining region or to make possible corrections. A definition of the focus point can be provided using coordinates in a patient coordinate system.

Due to the largely electronic adjustment via a control device, the use of the ultrasound device is clearly simplified for a physician or technician, such that errors that can have serious effects in the tumor treatment are avoided. A treatment plan that, for example, defines a series of focus points to be exposed to ultrasound in a tumor area can additionally be predetermined with the use of the control device. This plan can then be executed at a specific time. A diagnostic procedure with lower energies can additionally precede the treatment with the use of high energy densities when the transducer elements or transceiver elements are fashioned to transmit and receive in order to generate image exposures. Both a diagnosis at weaker energies and a subsequent treatment that is associated with the diagnostic after a suitable parameterization for the emission of the sound waves has been implemented are thus possible with the ultrasound device according to the invention. Higher energies are used for the treatment.

The sound intromission angle and/or a focus point for at least one (in particular all) transducer elements can be adjustable and/or variable and/or definable on the part of an operator. In addition to the completely automatic and/or semi-automatic adjustment of sound intromission angles and focus points by a control device (that for this purpose can access existing image exposures or data), a manual adjustment by an operator is alternatively or additionally possible. The manufacturer adjustment advantageously ensues in addition, for example for such cases in which an automatic detection of the suitable focus point by a control device is only possible with difficulty due to a complex structure of a tumor or—in which other problems of this type occur. For example, the focus point can be provided purely manually, or possibly supported by an image processing program, while the remainder of the adjustment of the individual transducer elements ensues via the electronic control.

According to the invention, the control device can be fashioned to vary the sound intromission angle and/or the focus point dependent on the application, in particular dependent on the desired strength and/or distribution of the sound field energy for a diagnosis and/or treatment. For example, an examination or treatment plan can be established in advance in this manner, which examination or treatment plan can, for example, be selected at a programming means of the control device and has as its content that diagnostic image exposures should initially be generated, using which image exposures the treatment should subsequently be conducted with the ultrasound device. In this case the control device can adapt the sound intromission angles or and focus points and the activation wholly automatically and/or dependent on inputs of an operator in order, for example, to obtain the lower energies that are required for image exposures while at the same time a larger area must simultaneously be covered in image exposures. The distribution of the field energy can thus be flexibly adapted to a specific application. It is also possible to alter the focus depths depending on the type of the treatment for a comprehensive tumor treatment with various focus points.

The measurement device of the ultrasound device can be part of the transducer, thus is incorporated into the flexible carrier, wherein the measurement device can be formed by one or more transducer elements fashioned for reception or represents a mere reception element at one or more positions, or is fashioned for transmission and reception. Other techniques can additionally be used for position determination.

The ultrasound device (possibly the control device of the ultrasound device) can be fashioned to determine the times and/or time differences for an activation of the transducer elements dependent on a determined distance and/or a rotation of the transducer elements relative to a reference point, such that a desired sound field is generated. The times or, respectively, the time differences with which the individual transducer elements must be activated in order to obtain a sound field that, for example, is focused on one point and generates at this point the required or desired high energy density that is suitable to destroy a tumor (for example in the brain of a patient) are thus advantageously determined with the aid of a control device that for this possesses a suitable program means. The required "focal laws" are thus determined that predetermine the activation of the transducer elements. The time differences with which the focusing onto a given point at given angles is achieved are determined for the activation of the individual elements with the "focal laws". The separation of the elements is determined via the afore-mentioned measurement device, wherein alternatively or additionally a determination of distances and rotations of the individual transducer elements can ensue from older data of the patient, for example from data of the appertaining body part such as images or the like acquired with different modalities. Data from databases or the like can be drawn upon from which a sufficiently precise establishment of the distances and rotations for a specific body part can be derived, for example for diagnostic tasks.

The time differences can be determined relative to a time possibly set to zero, which time is associated with the transducer element with the shortest distance from a give focus point. In this case the timing is predetermined by the target (thus by the focus point) that was selected for the treatment, such that the positive relative times can be determined relative to this shortest delay. The offset times for the remaining transducer elements are determined relative to the time set to zero.

According to the invention, the transducer elements and/or the frequency and/or the energy of the ultrasound radiation can be modifiable dependent on the application. Thus some or all transducer elements of the carrier matrix can possibly be exchanged or activated in a different manner, for example such that the control device effects an activation of only a limited number of elements with a smaller sound emission. The frequencies and energies as well as the selection of the transducer elements depend on the desired area of use (thus on the body part that should be treated) or on the type of the application, thus whether a diagnostic use of the ultrasound device or an application for tumor treatment or the like is intended.

The flexible carrier can be formed at least in part of rubber and/or a rubber-containing and/or rubber-like material and/or a flexible plastic. Carriers are conceivable that are designed from suitable material combinations or, respectively, possible different material regions in order to possibly be more flexible in regions in which a greater curvature is expected than in regions that are fashioned largely flat, given the predominant majority of the patients under consideration. Naturally, additional materials not cited here can be used that exhibit the necessary flexibility for suitable alignment of the ultrasound transducer elements. If it is formed of rubber or the like, the flexible carrier can be adapted to various patients in that the flexible properties of the material are utilized.

The transducer can have, for instance, 10 to 1000 transducer elements, in particular 128 or 256 transducer elements. The specified numerical range is to be understood as an example, wherein the selection of many transducer elements possesses the advantage of a very flexible possible activation such that, even given very difficult-to-access treatment regions (for example tumors close to healthy tissue that may in no case be damaged), a treatment is enabled in that a suitable number of elements is possibly used in a specific activation sequence for acoustic irradiation. Typical or desirable numbers of transducer elements are 128 or 256 elements that can be incorporated into a rubber-like carrier or the like.

The flexible carrier can be fashioned or preformed to adapt to a curved body surface (in particular to the head surface) of a patient. Carriers are conceivable that, for example, are fashioned for treatment of the brain in the manner of bathing caps that are placed on the respective patient. An arrangement of the transducer elements at flexible positions that are predetermined by the specific anatomy of the patient therefore result given the ultrasound device according to the invention. An exact sound intromission into the body is thereby enabled that was previously not conceivable. It is thus possible to use ultrasound to destroy tumors since the focus point can be set with high precision, with the result that the high energy density that is harmful to the tissue is achieved only at the points preselected for destruction. With the ultrasound device according to the invention, a completely new field of use is thereby opened for ultrasound.

Moreover, the invention concerns a method for determining an activation for an ultrasound device, in particular as described in the preceding, with a transducer that possesses multiple transducer elements. The transducer elements are carried in a flexible carrier, in particular in a carrier fashioned to adapt to a curved surface, wherein the distances and rotations of the transducer elements are determined by means of a measurement device and times and/or time differences for the activation of the transducer elements are determined dependent on said distances and rotations, such that upon activation of the elements an ultrasound field with predetermined properties (in particular with regard to at least one focus point and/or sound intromission angle and/or at least one energy and/or frequency) is generated.

A position of transducer elements thus initially ensues in a flexible manner in the framework of the method according to the invention, for example via placement of a (possibly extensible) rubber carrier on a curved surface which can, for example, be a body surface of a patient. Distances and rotations of the transducer elements are subsequently determined with the aid of a measurement device in that ultrasound radiation or other signals are emitted and received by one or more receivers of the measurement device. For example, a determination of the distances and rotations can be effected dependent on a reference point. From these the times or time differences ("focal laws") can be determined that are required for an activation of the transducer elements so that an ultrasound field is generated with properties such as specific energy density at a specific focus point.

The determination of this desired activation for generation of the ultrasound field can ensue automatically by means of a control device, possibly dependent on determined specifications or an inspection or confirmation by a technician or natural scientist. The method can be used in the medical field or outside of the medical field, wherein given use for diagnostics or tumor treatment etc. in medicine the actual acoustic irradiation can be implemented in connection with the method (for example by a physician) after the determination of the required activation to achieve the desired goal, which determination forms the basis of the method. It is also conceivable to determine the required activation in order to later obtain the desired ultrasound field with the required energies or frequencies not by application of the carrier on the patient but via calculations, for example by means of a control device. For this purpose, images of the patient or database images and information can possibly be accessed with whose help the placement of the flexible carrier with the transducer elements is simulated.

A flexible usage of group radiators (for, among other things, the treatment of tumors but also for diagnostics) with a precise generation of the desired ultrasound fields is ultimately enabled via the use of the flexible carrier for the transducer elements.

DESCRIPTION OF THE PREFERRED EMBODIMENTS

Figure 1:
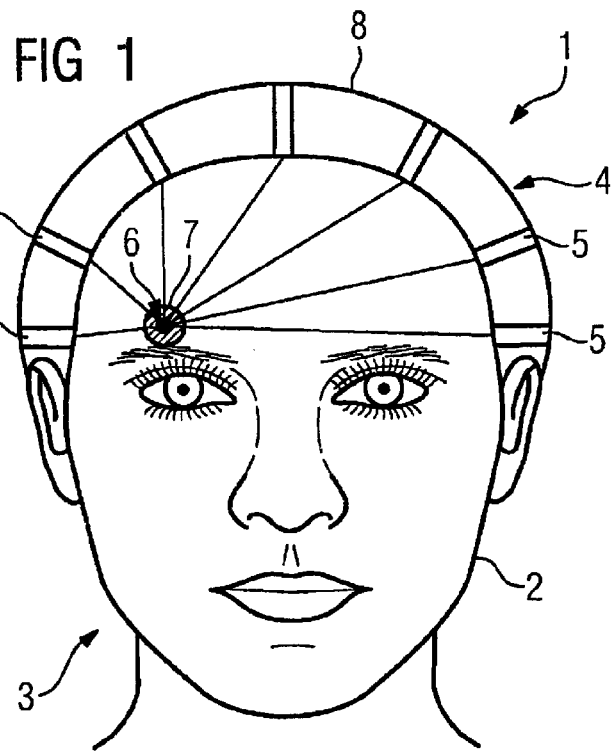
FIG. 1 schematically illustrates an ultrasound device according to the invention, with a carrier placed on the head of a patient.

An ultrasound device according to the invention, with a carrier resting on the head 2 of a patient 3, is presented in FIG. 1. The ultrasound device 1 has a transducer 4 that is formed by a plurality of transducer elements 5 (of which only a selection is presented here). The individual transducer elements 5 are fashioned dependent on its activation for emission of ultrasound at specific sound intromission angles such that the ultrasound is focused on a focus point 6.

The focus point 6 that is irradiated by the transducer elements 5 is located in a tumor 7 that was in turn established in the head 2 of the patient. The transducer elements 5 are incorporated into a flexible carrier 8 of the ultrasound device 1 that consists of a rubber-like material. With the aid of the flexible carrier 8, the transducer elements 5 can be positioned like a bathing cap on the head 2 of the patient 3. The coupling of the ultrasound ensues by means of gel or, respectively, water, for example in a water bath.

The sound field generated by the transducer elements 5 of the ultrasound device 1 can be varied in focus and angle so that both a diagnostic at weak energies and a subsequent treatment after a diagnostic and the defining parameterization of the "focal laws" (that predetermine the times or, respectively, time differences for the activation of the transducer elements 5) with increased energy are possible.

An exact sound intromission into the desired body region can thus ensue with the aid of the ultrasound device 1 according to the invention, which—due to the flexible carrier 8—offers the advantage that the transducer elements 5 can be variably adapted in terms of their position to the individual body surface of the patient 3. An exact setting is thereby achieved via the wholly novel concept of the flexible carrier 8 in combination with the phase array technique of electronic adjustment of the sound intromission angle or focus point of the transducer elements 5. The determination of the "focal laws" ensues by means of a measurement device that is integrated into the transducer 4 and fashioned to receive ultrasound signals. The distances and rotations of the individual transducer elements 5 relative to one another or relative to a reference point can thus be determined. Individual transducer elements 5 can be fashioned for transmission and reception for this and for diagnostics.

Figure 2:
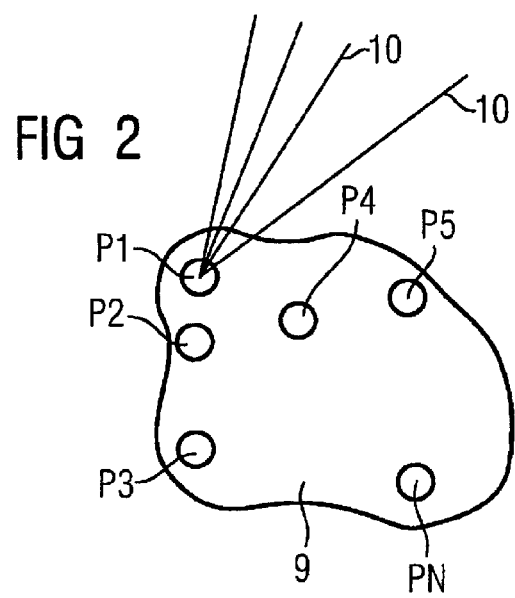
FIG. 2 illustrates a design for irradiation of a tumor with an ultrasound device according to the invention.

FIG. 2 shows a diagram for irradiation of a tumor with an ultrasound device according to the invention. The tumor 9 has different points P1 through PN which are desired focus points for an ultrasound treatment. The sound intromission angles and focus depths that are achieved via emission of ultrasound via the individual transducer elements are electronically varied with the aid of an ultrasound device as it is presented in FIG. 1. In the shown case an exposure of the selected focus point P1 occurs by interaction with the ultrasound beams that are radiated from different directions of the transducer elements of a flexible carrier (not shown here). If a specific target is defined (here thus the focus point P1), the transducer element is determined that possesses the shortest sound route relative to this zero point of the delay. The sound delay of this element with the shortest distance is set to zero; the offset times for the other transducer elements are thereupon calculated relative to this time. The required frequencies and energies depend on the usage area. In the shown case, a destruction of tumor tissue should occur, such that the focus points P1 through PN are successively irradiated with high energies.

Figure 3:
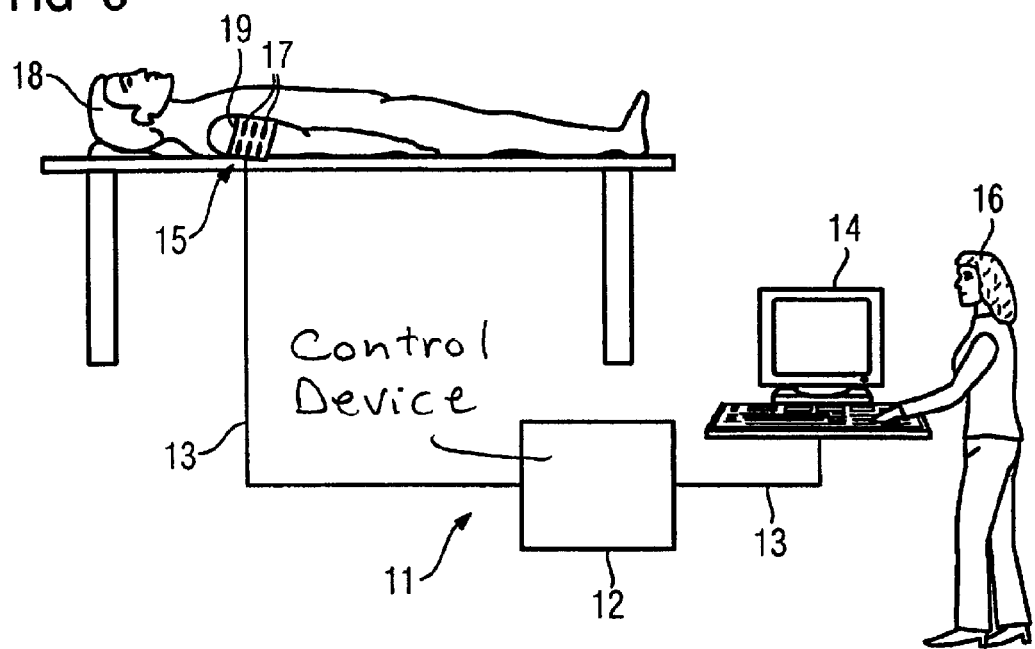
FIG. 3 illustrates a design for use of the ultrasound device according to the invention for diagnostics and treatment.

FIG. 3 shows a diagram for usage of an ultrasound device 11 according to the invention for diagnostics and treatment. The ultrasound device 11 has a control device 12 that is connected via corresponding lines 13 both with an image output and input device 14 and with the transducer 15 of the ultrasound device 11. An operator 16 who monitors the activation of the transducer 15 that is calculated in a suitable manner with the aid of the control device 12, dependent on the operator's specifications, is shown the image output and input device 14. This can possibly ensue such that a natural scientist is initially used as an operator 16 for the determination of the actual activation while subsequently a tumor treatment or a diagnostic is implemented under monitoring by a physician.

The transducer 15 has various transducer elements 19, of which here only a few are indicated. The transducer elements 19 are fashioned for transmission and reception of ultrasound. The transducer elements 19 are accommodated in a flexible carrier 17 that here rests on the curved upper arm or, respectively, shoulder region of a patient 18.

Specifications for the diagnostic and treatment to be implemented with the ultrasound device 11 are acquired with the use of a program that the operator 16 operates via the image output and input device 14 and are processed by the control device 12. The treatment ensues dependent on these specifications, which determine in which manner ultrasound exposures of the treatment region of the patient 18 should be produced that are subsequently automatically processed via calculation steps of the control device 12 to determine suitable focus points for a tumor treatment. The individual activation of the transducer elements 19 thus enables an exact acoustic irradiation of the patient 18 in connection with the flexible carrier 17 in which the transducer elements 19 of the transducer 15 are incorporated. Unwanted tissue damage can thus be largely precluded. It is thereby possible to use ultrasound devices such as the shown ultrasound device 11 in a significantly broader scope than before.

Figure 4:
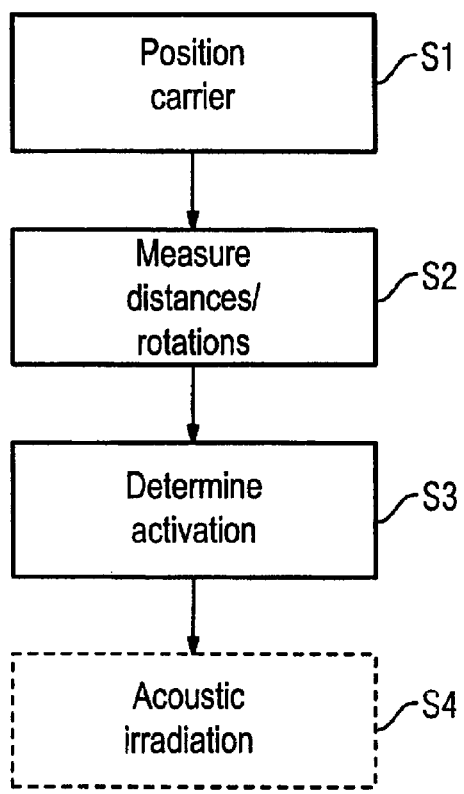
FIG. 4 is a flowchart of an embodiment of the method according to the invention.

A flowchart of a method according to the invention is shown in FIG. 4. In Step S1 the carrier with the transducer elements incorporated therein (which transducer elements can be exchanged or activated differently depending on the desired application field) is thereby initially positioned, for example on a body surface or another surface. In Step S2 a measurement method is implemented with which the distances and rotations of the transducer elements are determined relative to reference specifications or, respectively, relative to one another.

Finally, the activation of the ultrasound device such that a desired ultrasound field is generated is determined in Step S3. This occurs by the times or time differences for the activation of the transducer elements being calculated so that the desired sound field results. A control device can implement the desired acoustic irradiation (as indicated in the optional step S4) with the aid of these times. The determination of the activation can thereby ensue separate from the subsequent acoustic irradiation, such that the activation is (for example) determined by a medical technology assistant while the acoustic irradiation itself is implemented under monitoring by a physician. In other application fields the acoustic irradiation can be integrated into the method, wherein a wholly automatic method workflow can be achieved with the use of a control device after positioning of the carrier.

Although modifications and changes may be suggested by those skilled in the art, it is the intention of the inventor to embody within the patent warranted hereon all changes and modifications as reasonably and properly come within the scope of his contribution to the art.

I claim as my invention:

1. An ultrasound device for treating a pathology located at a treatment site of a patient, comprising:
   a transducer comprised of a plurality of transducer elements, each transducer element being individually activatable to emit ultrasound;
   a flexible carrier to which said transducer elements are mounted, said flexible carrier being configured for placement of said transducer elements on the patient;
   a measurement device configured to determine respective distances and rotations of said transducer elements with respect to the treatment site, after placement of the transducer elements and said carrier on the patient; and
   a control device configured to determine respective times or time differences for respective activation of said transducer elements dependent on the determined distance and rotation of the respective transducer elements relative to said treatment site to produce an ultrasound field at said treatment site that is a simultaneous convergence of the respective ultrasound emitted by the respective transducer elements, and to operate said transducer to activate the respective transducer elements at said respective times or time differences.

2. An ultrasound device as claimed in claim 1 wherein said control unit is configured to electrically set, for each of said transducer elements, at least one of a sound intromission angle and a focus point for the ultrasound emitted therefrom.

3. An ultrasound device as claimed in claim 2 wherein said control unit is configured to electronically said at least one of said sound intromission angle and said focus point for at least one of said transducer elements in response to an operator input into said control unit.

4. An ultrasound device as claimed in claim 2 wherein said control unit is configured to set at least one of said sound intromission angle and said focus point dependent on a predetermined characteristic, selected from the group consisting of signal strength and an ultrasound field energy distribution at said treatment site treatment.

5. An ultrasound device as claimed in claim 1 wherein measurement device is a part of said transducer.

6. An ultrasound device as claimed in claim 1 wherein said control device is configured to determine said times or time differences relative to a time that is set to zero for each transducer element, representing a shortest distance from a focus point for that transducer element.

7. An ultrasound device as claimed in claim 1 wherein each of said transducer elements operates to emit ultrasound at a frequency and at an energy, and wherein said control unit is configured to operate said transducer to selectively modify at least one of said frequency and said energy.

8. An ultrasound device as claimed in claim 1 wherein said flexible carrier is at least partially comprised of a material selected from the group consisting of rubber, rubber-containing materials, and flexible plastic materials.

9. An ultrasound device as claimed in claim 1 wherein said transducer comprises 10 to 1000 of said transducer elements.

10. An ultrasound device as claimed in claim 1 wherein said transducer comprises a plurality of said transducer elements selected from the group consisting of 128 transducer elements and 256 transducer elements.

11. An ultrasound device as claimed in claim 1 wherein said flexible carrier is configured to adapt to a curved body surface of the examination subject.

12. A method for, comprising the steps of:
forming a transducer comprised of a plurality of transducer elements, each transducer element being individually activatable to emit ultrasound;
mounting said transducer elements to a flexible carrier;
configuring said flexible carrier for placement of said transducer elements on the patient and placing said transducer elements mounted on said flexible carrier on the patient;
in a measurement unit, automatically determining respective distances and rotations of said transducer elements with respect to the treatment site, after placement of the transducer elements and said carrier on the patient; and
in a control unit automatically determining respective times or time differences for respective activation of the transducer elements dependent on the determined distances and rotations thereof relative to said treatment site; and
from said control unit, respectively activating said transducer elements at said times or time differences to emit ultrasound therefrom having a characteristic dependent on said times or time differences selected from the group consisting of a focus point, a sound intromission angle, an energy, and a frequency, to produce an ultrasound field at said treatment site that is a simultaneous convergence of the respective ultrasound emitted by the respective transducer elements.

* * * * *